United States Patent
Bichay

(10) Patent No.: US 7,728,315 B2
(45) Date of Patent: *Jun. 1, 2010

(54) RADIATION ATTENUATION CORRIDOR

(75) Inventor: Tewfik J. Bichay, Rockford, MI (US)

(73) Assignee: Trinity Health Corporation, Novi, MI (US)

(*) Notice: Subject to any disclaimer, the term of this patent is extended or adjusted under 35 U.S.C. 154(b) by 0 days.

This patent is subject to a terminal disclaimer.

(21) Appl. No.: 11/868,658

(22) Filed: Oct. 8, 2007

(65) Prior Publication Data

US 2008/0023658 A1 Jan. 31, 2008

Related U.S. Application Data

(63) Continuation of application No. 11/183,508, filed on Jul. 18, 2005, now Pat. No. 7,291,854.

(51) Int. Cl.
G02B 5/00 (2006.01)
G21K 1/00 (2006.01)
H01J 1/52 (2006.01)
H01J 3/00 (2006.01)
H01J 5/18 (2006.01)
H01J 29/46 (2006.01)
G21C 11/00 (2006.01)
G21F 3/02 (2006.01)

(52) U.S. Cl. ............... 250/517.1; 250/505.1; 250/515.1

(58) Field of Classification Search ............... 250/505.1, 250/515.1, 517.1, 492.1, 455.11, 506.1
See application file for complete search history.

(56) References Cited

U.S. PATENT DOCUMENTS 1,609,682 A 12/1926 Angebaud (Continued)

FOREIGN PATENT DOCUMENTS

JP 02077698 A 3/1990

(Continued)

OTHER PUBLICATIONS

Naquin et al. ("A Low Gamma Dose Rate Cobalt-60 Facility" Radiation Protection Management, Mar./Apr. 2001, vol. 18, No. 2, pp. 31-36).*

(Continued)

*Primary Examiner*—Jack I Berman
*Assistant Examiner*—Brooke Purinton
(74) *Attorney, Agent, or Firm*—Robert L. Kelly; Dickinson Wright PLLC

(57) ABSTRACT

A radiation attenuation corridor couples a radiation therapy room and a control room. The radiation attenuation corridor is made of a material that substantially absorbs ionizing radiation and substantially blocks the transmission of the ionizing radiation. Specific wall portions at the entrance of the corridor are covered with borated polyethylene (BPE). Specific wall portions diverge from an axis defined by the corridor by from about 10 degrees to about 45 degrees. The corridor thus leads out of the room and angles laterally across the wall of the therapy room, before angling again and opening to a safe room. The added angles in the radiation corridor increase the distance of radiation travel, and make the path more indirect, thereby increasing the contact of the radiation emissions with the radiation shielding and further attenuating the radiation.

1 Claim, 2 Drawing Sheets

U.S. PATENT DOCUMENTS

| | | | |
|---|---|---|---|
| 1,780,108 | A | 10/1930 | Barry |
| 2,853,624 | A | 9/1958 | Wigner et al. |
| 3,299,270 | A | 1/1967 | D'Avella |
| 3,517,627 | A | 6/1970 | Kruse |
| 3,564,241 | A | 2/1971 | Ludwig |
| 4,038,553 | A | 7/1977 | McCullagh |
| 4,074,141 | A | 2/1978 | Bryant |
| 4,400,623 | A | 8/1983 | Jacobson |
| 4,514,640 | A | 4/1985 | Bagnell et al. |
| 4,638,166 | A | 1/1987 | Baudro |
| 4,833,335 | A | 5/1989 | McGinley et al. |
| 5,422,704 | A * | 6/1995 | Sego .................. 355/53 |
| 6,183,243 | B1 | 2/2001 | Snyder |
| 7,107,778 | B1 * | 9/2006 | Witham et al. ............ 62/264 |
| 7,274,026 | B2 * | 9/2007 | Bol et al. ............ 250/453.11 |
| 7,417,239 | B2 * | 8/2008 | Naslund et al. ......... 250/492.1 |
| 2006/0105700 | A1 * | 5/2006 | Hadlock, Jr. ............ 454/270 |

FOREIGN PATENT DOCUMENTS

| | | | |
|---|---|---|---|
| JP | | 05223987 A | 9/1993 |

OTHER PUBLICATIONS

Peter J. Biggs Ph.D., Radiation Shielding for Megavoltage Therapy Machines in the Post-NCRP 49 Era, AAPM Refresher Course, Jul. 19, 2001, pp. 4-20, Department of Radiation Oncology, Massachusetts General Hospital, Harvard Medical School, Boston, MA 02114.

Petter J. Biggs Ph.D., The New Radiation Shielding Methodologies for Medical Imaging and Therapy—A Primer for the Next 30 Years, SEAAPM, Mar. 3-4, 2005, Massachusetts General Hospital, Harvard Medical School, Boston, MA 02114.

K.J. Riley et al., A state-of-the art epithermal neutron irradiation facility for neutron capture therapy, Phys. Med. Biol. 49 (2004) 3725-3735, Institute of Physics Publishing, Printed in the UK.

D.J. Dawson, LRCP Doorless Entry System, Medical Physics, Feb. 1998, vol. 25, No. 2, American Association of Physicists in Medicine, Department of Physics, London Regional Cancer Centre, Cancer Care Ontario, 790 Commissioners Rd. E., London, Ontario, Canada, N6A 4L6.

* cited by examiner

RADIATION ATTENUATION CORRIDOR

CROSS REFERENCE TO RELATED APPLICATION

This application is a continuation of and claims priority to U.S. application Ser. No. 11/183,508 filed on Jul. 18, 2005 entitled "Radiation Attenuation Corridor".

TECHNICAL FIELD

The present invention relates generally to radiation shielding and particularly to an improved radiation attenuation corridor for radiation treatment facilities.

BACKGROUND OF THE INVENTION

Radiation therapy utilizes several types of ionizing radiation, such as beta-rays, gamma rays and x-rays, as well as high-energy protons and neutrons applied to malignant tissue to prevent and control the spread of cancer. While ionizing radiation is capable of destroying cancerous tissue, it is also capable of damaging healthy tissue inadvertently exposed thereto. Thus, a necessary precondition for treatment is the safeguard of patients and personnel from accidental radiation exposure.

Various methods of shielding radiation in rooms and walls are known and in use in hospitals around the world. However, most of these methods are expensive to manufacture and can be complicated to use. Many use complex "radiation mazes" composed of thick leaded walls with multiple 90-degree turns, capped off with a heavy leaded door, often weighing thousands of pounds. Typically, the many walls are composed of thick concrete or other materials known for their ability to absorb or block ionizing radiation. These methods have several drawbacks. The heavy doors require mechanized assistance through automated motors and the like. This is both time consuming and dangerous, as technicians and patients alike can get caught in the door if they are not careful. Furthermore, it is time consuming for a therapist whenever the patient requires adjustment or assistance. Moreover, the closing of a thick lead door has a negative psychological impact on the patient who can feel entombed in the therapy room. Additionally, such a room is expensive and the required footprint is very large, resulting in a lot of unusable space. Finally, it has been known for these heavy doors to become stuck in the closed position due to motor or hinge failure. The patient is then alone in the treatment room and must await for the heavy door to be opened by some other means.

Some radiation therapy rooms have been created with a doorless entry system. See, Dawson et al., in "Doorless Entry System", Medical Physics, fol. 25, No. 2 (February 1998), the entire disclosure and subject matter of which is hereby incorporated herein by reference. While such a system meets some of the above identified challenges, it is desired to increase the radiation attenuation, by improving the system geometry.

SUMMARY OF THE INVENTION

What is needed therefore is an improved radiation corridor that substantially absorbs ionizing radiation and substantially blocks the transmission of ionizing radiation from inside a room containing a radiation source, takes up as little room as possible, and is cost-efficient. Additionally, it is desirable to avoid the need for a heavy mechanized door.

The present disclosure comprises a radiation attenuation corridor coupling a radiation therapy room and a safe area. The safe area is useful as, for instance, a control room wherefrom a therapist can operate radiation therapy controls to administer radiation to a patient, or other common area.

A preferred radiation corridor in accordance with the present disclosure basically comprises a corridor which is open at one end to a radiation therapy room and is open at another end to a control room or other site. The corridor comprises a first wall and a second wall, a floor and a ceiling, all made of a material that substantially absorbs ionizing radiation and that substantially blocks the transmission of the ionizing radiation. The first wall and the second wall portions are substantially parallel and diverge from an axis defined by the corridor by from about 10 degrees to about 45 degrees. The corridor thus leads out of the room and makes a 90 degree turn. The corridor then turns at an obtuse angel to traverse laterally across the wall of the therapy room, before turning at a second obtuse angle in the opposite direction of the first. Finally, the corridor makes another 90 degree turn before opening to a safe area.

In a preferred embodiment, selected portions of the walls of the corridor are lined with radiation attenuation materials, including, but not limited to, wood, plastics, polyethylene, graphite, wax, water or other suitable materials high in hydrogen concentration. In a further preferred embodiment, the radiation attenuation material is borated polyethylene (BPE).

The placement of the angles in the radiation corridor increases the distance radiation must travel, and makes the path more indirect. This increases the contact the radiation emissions with the radiation shielding. In other words, the ionizing radiation bounces between wall sections until it is absorbed before reaching the outer door openings. Coupling this novel geometry with the placement of BPE attenuates the radiation to a point where a door is not necessary for blockage of radiation.

BRIEF DESCRIPTION OF THE DRAWINGS

The present invention will now be described, by way of example, with reference to the accompanying drawings, in which.

DESCRIPTION OF THE PREFERRED EMBODIMENT

Figure 1:
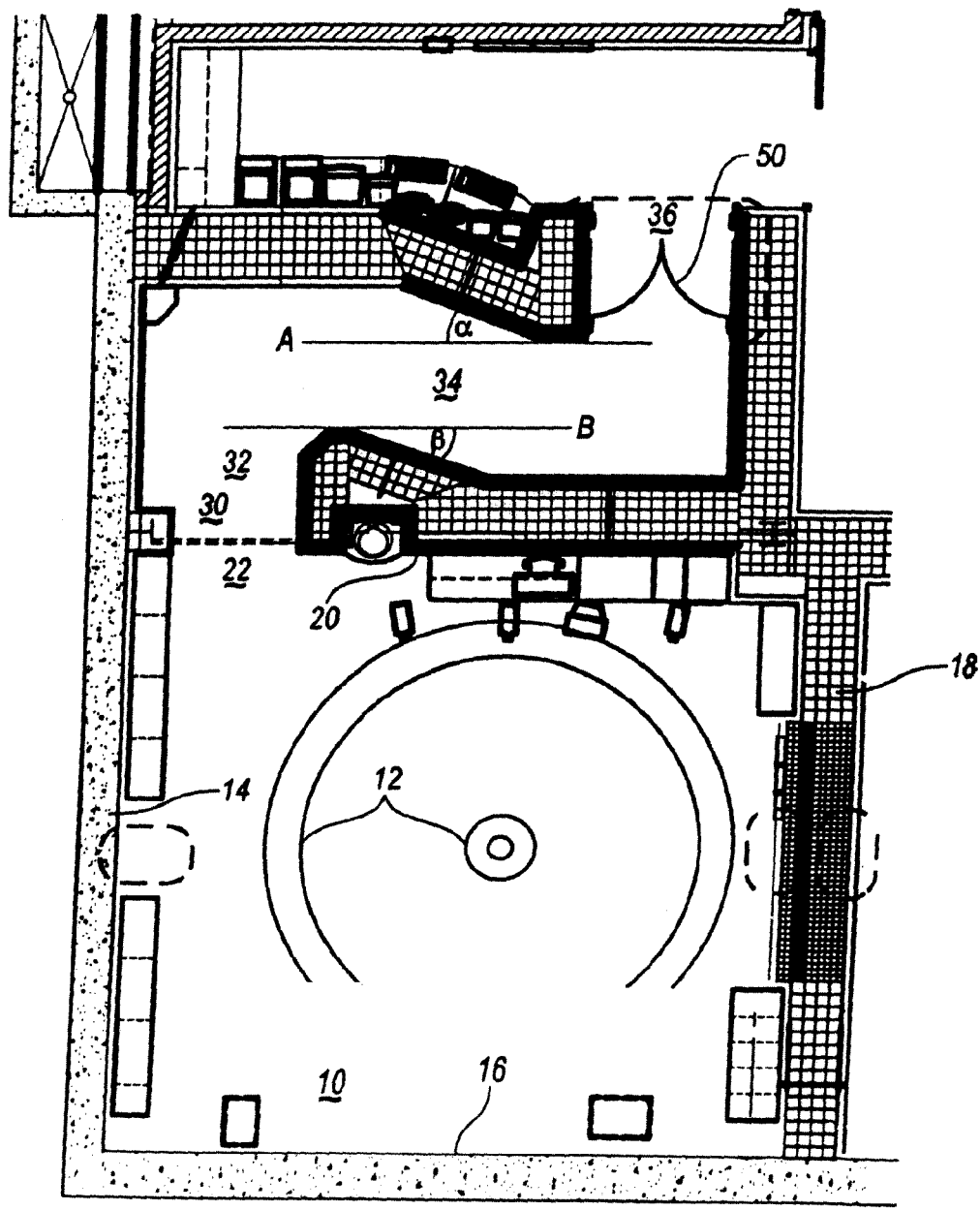
FIG. 1 illustrates a schematic view of a radiation therapy area incorporating a radiation attenuation corridor according to one embodiment of the present disclosure.

Referring now to the drawings, preferred embodiments of the present invention are shown in detail. Although the drawings represent embodiments of the present invention, the drawings are not necessarily to scale and certain features may be exaggerated to better illustrate and explain the present invention. The embodiments set forth herein are not intended to be exhaustive or to otherwise limit the invention to the precise forms disclosed in the following detailed description.

Figure 2:
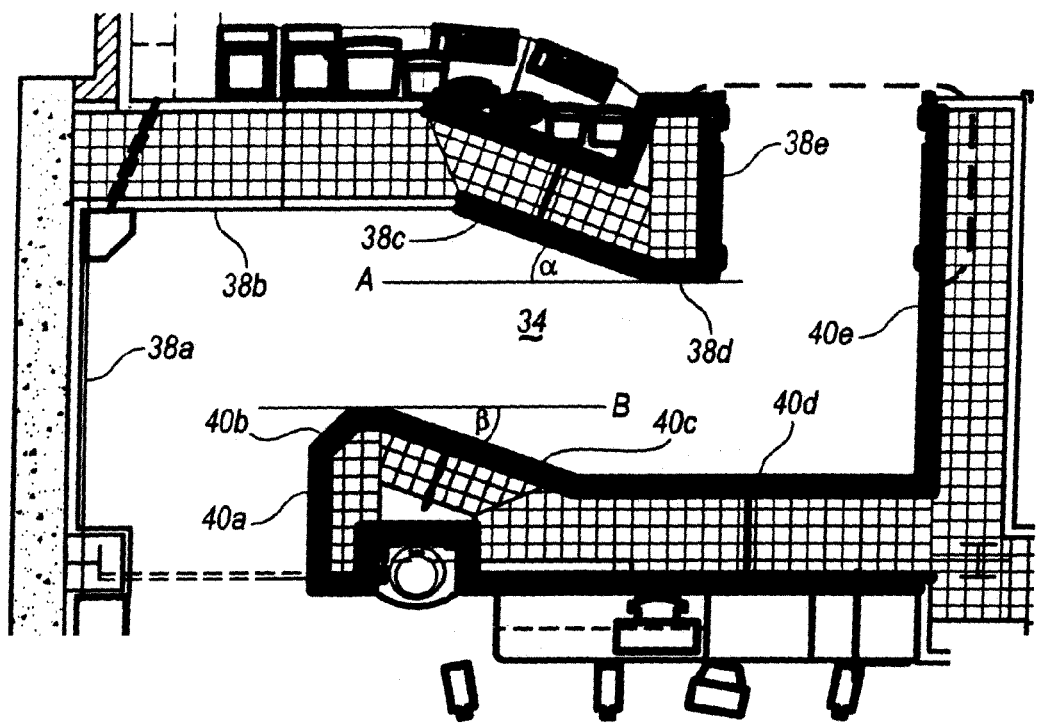
FIG. 2 illustrates a schematic view of a radiation attenuation corridor according to another embodiment of the present disclosure.

Referring now to FIGS. 1 and 2, therapy room 10 includes a radiation source 12, a first wall 14, a second wall 16 a third wall 18 and a fourth wall 20. Fourth wall 20 includes an opening 22 leading to an access corridor 30, which extends along the first wall 14 away from the therapy room 10.

Access corridor 30 comprises a therapy room access portion 32, an angular traverse portion 34, and a control room access portion 36, and is defined throughout by a first corridor wall 38a-38e, a second corridor wall 40a-40e, a floor and a ceiling. The first corridor wall 38a-38e, second corridor wall 40a-40e, floor and ceiling are made of materials that substantially absorb ionizing radiation and that substantially block the transmission of the ionizing radiation. In a preferred embodiment, wall section 38a has a length from about 5 ft. to about 22 ft., wall section 38b has a length from about 5 ft. to about 20 ft., wall section 38c has a length from about 3 ft. to about 15 ft., wall section 38d has a length from about 1 ft. to about 5 ft. and wall section 40a has a length from about 2 ft. to about 10 ft., wall section 40b has a length from 1 ft. to about 5 ft., wall section 40c has a length from about 3 ft. to about 12 ft., wall section 40d has a length from about 5 ft. to about 20 ft., and wall section 40e has a length from about 5 ft. to about 20 ft.

Corridor wall portions 38a and 38b meet at the junction of the therapy room access portion 32 and the angular traverse portion 34. First corridor wall portions 38a and 38b are lined with BPE, much in the matter that wall insulation is inserted between wall studs. They have a preferred length about 4 ft. to about 15 ft. In one preferred embodiment, first corridor wall portions 38a and 38b are lined with BPE for a length of 8 feet in either direction from their junction point.

The therapy room access portion 32 opens at one end into the therapy room 10 along the fourth wall 20, and extends outward from the therapy room 10 a given distance. The therapy room access portion 32 is then coupled with the angular traverse portion 34 of the access corridor 30 at the corner. The angular traverse portion 34 traverses a portion of the fourth wall 20 while angling toward the interior of the therapy room 10. That is, the angular traverse portion 34 forms a first acute angle with the therapy room access portion 32. The angle, α, between axis A and first corridor wall portion 38c may be from 10 to 45 degrees. Similarly, the angle, β, between axis B and second corridor wall portion 40c may be from 10 to 45 degrees. Axis A and axis B are preferably substantially parallel, and relate generally to the axis defined by the corridor. The first corridor wall portion 38c and the second corridor wall portion 40c of the angular traverse portion 34 can be parallel, such that angles α and β are identical, or they can converge, such that angle α is greater than angle β. The angular traverse portion 34 is then coupled with the control room access portion 36 at another corner, and the control room access portion 36 leads further away from the center of the therapy room 10. The angular traverse portion 34 forms a second acute angle with the control room access portion 36. In one preferred embodiment, the first acute angle and the second acute angle are such that the therapy room access portion 32 and the control room access portion 36 are substantially parallel, though other embodiments are contemplated depending on the specific application. In a most preferred embodiment, the distance between opposing walls is a minimum of six feet, to allow for the easy transfer of both patients and equipment into, and out of, the radiation therapy room.

In one preferred embodiment, an access door 50 is included at the end of the control room access portion 36 to prevent unauthorized or inadvertent access to the therapy room 10. In such an embodiment, sensors responsive to movement can be integrated with the door 50 to shut off the supply of radiation when someone enters the corridor 30.

In a further preferred embodiment, in which the door is absent, one or more proximity sensors (not shown) are located at the junction of the control room and the control room access portion 36 to detect entry into the access corridor 30. Upon detection of entry into the access corridor 30, the system could be set to shut down the radiation, to prevent injury to the entrant. Furthermore, one or more proximity sensors can be employed near the junction of the control room and the control room access portion, such that an audible or a visual warning can be given when someone nears the control room access portion. This can prevent inadvertent access to the control room access portion, thereby preventing the need to shut down the radiation, and save time for the therapist and patient.

It is to be understood that the above description is intended to be illustrative and not limiting. Many embodiments will be apparent to those of skill in the art upon reading the above description. Therefore, the scope of the invention should be determined, not with reference to the above description, but instead with reference to the appended claims, along with the full scope of equivalents to which such claims are entitled. The disclosures of all articles and references, including patent applications and publications cited herein are incorporated herein by reference for all purposes.

Initial tests done on an embodiment of the doorless radiation attenuation corridor as described above have been performed, and the results are listed in the table below. These results compare favorably with currently mandated "acceptable" radiation levels, and demonstrate the viability of the disclosed system design.

| Rep Rate MU/min | Gantry | Energy (MV) | Field Size (cm) | Photons (μSv/hr) | Neutron (μSv/hr) | Instant Dose (μSv/hr) |
|---|---|---|---|---|---|---|
| 500 | 0 | 15 | 0 | 2.30 | 7.00 | 9.30 |
| 500 | 0 | 15 | 10 | 2.40 | 7.00 | 9.40 |
| 500 | 0 | 15 | 40 | 2.00 | 4.00 | 6.00 |
| 500 | 90 | 15 | 0 | 1.70 | 4.00 | 5.70 |
| 500 | 90 | 15 | 10 | 1.90 | 3.00 | 4.90 |
| 500 | 90 | 15 | 40 | 3.70 | 1.50 | 5.20 |
| 500 | 180 | 15 | 0 | 1.90 | 5.00 | 6.90 |
| 500 | 180 | 15 | 10 | 2.20 | 5.00 | 7.20 |
| 500 | 180 | 15 | 40 | 1.80 | 2.80 | 4.60 |
| 500 | 270 | 15 | 0 | 2.80 | 9.90 | 12.70 |
| 500 | 270 | 15 | 10 | 2.70 | 6.00 | 8.70 |
| 500 | 270 | 15 | 40 | 2.20 | 5.60 | 7.80 |

What is claimed is:

1. A doorless radiation attenuation corridor through which patients pass through to a room containing a source of radiation, said corridor comprising:

an entry corridor having walls, a ceiling and a floor made of radiation resistant materials, said entry corridor defining a first axis along which said patients pass from a safe region;

an intermediate corridor attached to said entry corridor, said intermediate corridor having walls, a ceiling and a floor made of radiation resistant materials, said intermediate corridor defining a second axis along which said patients pass, said second axis being at substantially a 90° angle to said first axis;

said walls of said intermediate corridor having portions which are substantially parallel to one another, said substantially parallel portions of said walls of said intermediate portions forming angles with said second axis of between 10° and 45°;

a final corridor leading to said room containing said radiation source, said final corridor having walls, a ceiling and a floor made of radiation resistant materials, said final corridor defining a third axis along which patients pass said third axis being at substantially a 90° angle to said second axis;

wherein radiation from said radiation source is substantially attenuated between said radiation source and said safe region in a doorless corridor.

* * * * *